(12) United States Patent
Fink et al.

(10) Patent No.: US 9,017,354 B2
(45) Date of Patent: Apr. 28, 2015

(54) MEDICAL CUTTING INSTRUMENT FOR SEVERING MUSCLES AND TENDONS

(75) Inventors: Christian Fink, Innsbruck (AT); Daniel Weinmann, Seitingen-Oberflacht (DE); Sascha Berberich, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 77 days.

(21) Appl. No.: 13/402,431

(22) Filed: Feb. 22, 2012

(65) Prior Publication Data

US 2012/0215240 A1 Aug. 23, 2012

(30) Foreign Application Priority Data

Feb. 22, 2011 (DE) .......................... 10 2011 012 014

(51) Int. Cl.
*A61B 17/32* (2006.01)
*A61B 17/00* (2006.01)
(Continued)

(52) U.S. Cl.
CPC ............ *A61B 17/32* (2013.01); *A61B 17/00008* (2013.01); *A61B 17/3211* (2013.01); *A61B 2017/00969* (2013.01); *A61B 17/3213* (2013.01)

(58) Field of Classification Search
CPC ............... A61B 2017/00761; A61B 2017/322; A61B 2017/3225; A61B 2017/00261; A61B 17/54; A61B 17/322; A61B 17/3211; A61B 17/32093; A61B 17/1604; A61B 17/1659; A61B 2019/481; A61B 9/0133; A47J 17/02; A22B 5/168; B26D 3/283; B26D 3/00; B26D 3/08; B26D 2003/285; B26D 9/02; B26D 5/005; B43M 7/002

USPC ............... 606/131–132, 167, 172, 79, 83, 84; 30/278, 280, 286, 287, 289, 294, 314

See application file for complete search history.

(56) References Cited

U.S. PATENT DOCUMENTS

| 697,902 A | * | 4/1902 | Tripp .............................. 83/455 |
| 1,830,692 A | * | 11/1931 | Becker ............................ 30/304 |
| 3,797,505 A | | 3/1974 | Gilhaus et al. |

(Continued)

FOREIGN PATENT DOCUMENTS

| DE | 8421587 U1 | 11/1984 |
| EP | 0470903 A1 | 2/1992 |

(Continued)

OTHER PUBLICATIONS

European Search Report; Application No. EP 12 00 1083; Issued: Apr. 27, 2012; 5 pages.

*Primary Examiner* — David Eastwood
(74) *Attorney, Agent, or Firm* — St. Onge Steward Johnston & Reens LLC

(57) ABSTRACT

A medical cutting instrument for cutting muscles and tendons, with an instrument body that includes a handle on its proximal end and at least one cutting knife in the area of its distal end. To provide a medical cutting instrument that guarantees ease of handling and simple structure along with secure cutting of the muscle/tendon tissue, the instrument body should be of grooved configuration in the area of its cutting knife in such a way that the instrument body includes a hollow space extending in the longitudinal direction of the instrument body to receive and guide the muscle/tendon tissue that is to be cut, such that the instrument body includes an opening extending in the longitudinal direction of the instrument body and the cutting knife constitutes a side of the instrument body.

7 Claims, 2 Drawing Sheets

(51) Int. Cl.
*A61B 17/3211* (2006.01)
*A61B 17/3213* (2006.01)

(56) References Cited

U.S. PATENT DOCUMENTS

| | | | |
|---|---|---|---|
| 4,239,045 A | 12/1980 | Schlein | |
| 5,026,385 A * | 6/1991 | Schutte et al. | 606/167 |
| 5,423,825 A * | 6/1995 | Levine | 606/86 R |
| 5,447,516 A * | 9/1995 | Gardner | 606/167 |
| 5,601,584 A * | 2/1997 | Obagi et al. | 606/172 |
| 5,951,580 A | 9/1999 | Ashraf | |
| 6,179,852 B1 * | 1/2001 | Strickland et al. | 606/167 |
| 6,261,265 B1 * | 7/2001 | Mosseri | 604/198 |
| 6,905,290 B1 * | 6/2005 | Casciato, Jr. | 407/29.15 |
| 7,255,705 B2 * | 8/2007 | Hsu et al. | 606/167 |
| 7,322,942 B2 | 1/2008 | Roe | |
| 7,900,362 B2 * | 3/2011 | Djordjevic et al. | 30/162 |
| 8,252,011 B1 * | 8/2012 | Forrester et al. | 606/167 |

FOREIGN PATENT DOCUMENTS

| | | |
|---|---|---|
| JP | 2010284478 A | 12/2010 |
| WO | 9611639 A1 | 4/1996 |
| WO | 9939632 A1 | 8/1999 |

* cited by examiner

1

MEDICAL CUTTING INSTRUMENT FOR SEVERING MUSCLES AND TENDONS

CROSS-REFERENCE TO RELATED APPLICATIONS

The present application claims priority of German patent application No. 10 2011 012 014.9 filed on Feb. 22, 2011, the content of which is incorporated herein by reference.

FIELD OF THE INVENTION

The invention relates to a medical cutting instrument for cutting muscles and tendons, with an instrument body that comprises a handle at its proximal end and a cutting knife in the area of its distal end.

BACKGROUND OF THE INVENTION

Medical cutting instruments of this type are used, for example, to prepare a tendon transplant in the event of a tear.

Patent DE 84 21 587 U1 discloses a generic medical cutting instrument configured as a tenotome. This known medical cutting instrument comprises a guide ring that is equipped with an opening mechanism and can be placed around the muscle/tendon tissue of the implant that is still fastened at both ends. To actuate the opening mechanism and then to cut the muscle/tendon tissue, the cutting knife is mounted in the instrument body so that it can be slid axially, such that the sliding takes place via an actuation ring positioned on the handle of the instrument body. The known instrument further comprises a blocking mechanism in order to prevent unintentional actuation of the cutting knife.

The known tenotome makes possible a precise preparation of a muscle/tendon implant, but the structure and operation of this known medical cutting instrument with the slidable opening mechanism and the additional blocking mechanism are highly complex.

SUMMARY OF THE INVENTION

Consequently it is the object of the invention to provide a medical cutting instrument of the aforementioned type that, in addition to ease of operation, ensures simple structure and secure cutting of muscle/tendon tissue.

The object is fulfilled, according to the invention, in that the instrument body in the area of the cutting knife has a grooved configuration in such a way that the instrument body comprises a hollow space extending in the longitudinal direction of the instrument body and serving to receive and guide the muscle/tendon tissue that it is to be cut, such that the instrument body comprises an opening extending in the longitudinal direction and the cutting knife constitutes one side of the instrument body.

Owing to the configuration of the instrument body as a grooved hollow body, it is possible in simple manner, without an additional guide mechanism, to guide the tissue that is to be cut in the area of the cutting knife in the correct position.

According to a preferred embodiment of the invention, it is proposed that the cutting knife on its distal side should comprise a cutting edge aligned diagonally to the longitudinal direction of the instrument body, so that the cutting edge can be used without disturbing the mounting of the tissue on the guide piece.

The proximal side of the cutting knife opposite the cutting edge, according to the invention, is advantageously configured running at an angle toward the open side of the instrument body in order to enable lateral incision into the bundle of tendons that is to be cut.

Incision into a muscle or tendon tissue bundle that is to be cut is further facilitated according to the invention by the fact that the cutting knife overlaps the instrument body in the direction perpendicular to the instrument's longitudinal axis.

With a practical embodiment of the invention, it is proposed that the cutting knife should constitute a side of the instrument body that borders the opening of the instrument body, such that the distance between the cutting knife and the other side of the instrument body, which is opposite the cutting knife and also borders the opening of the instrument body, is adjustable to allow various cutting depths to be selected.

The guide track for the muscle/tendon tissue that is to be cut constitutes, according to the invention, the inside of the instrument body that is opposite the opening of the instrument body.

According to a first practical embodiment for configuring the instrument body, it is proposed with the invention that the instrument body should be configured as a rectangular profile.

Finally, with a second inventive embodiment it is proposed that the instrument body should be configured as curved in cross-section, preferably rounded.

Additional characteristics and advantages of the invention can be seen from the appended drawings, in which an embodiment of an inventive medical cutting instrument for cutting muscles and tendons is illustrated merely by way of example, without restricting the invention to that embodiment.

DETAILED DESCRIPTION OF THE INVENTION

Figure 1:
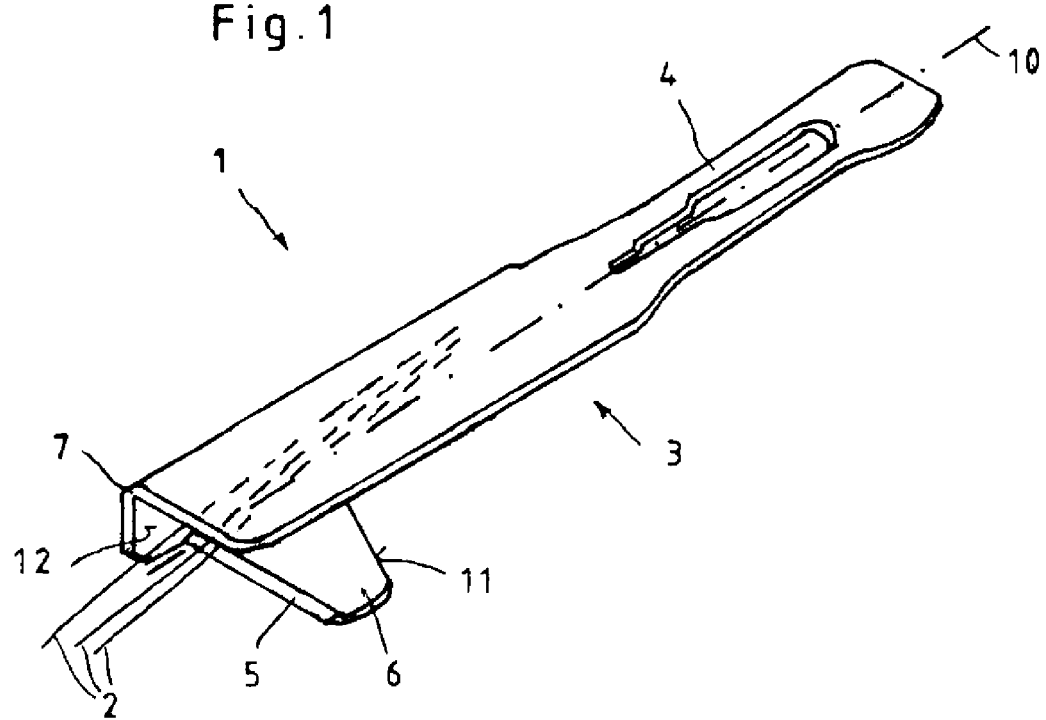
FIG. 1 shows a perspective side view of an inventive medical cutting instrument.
Figure 2:
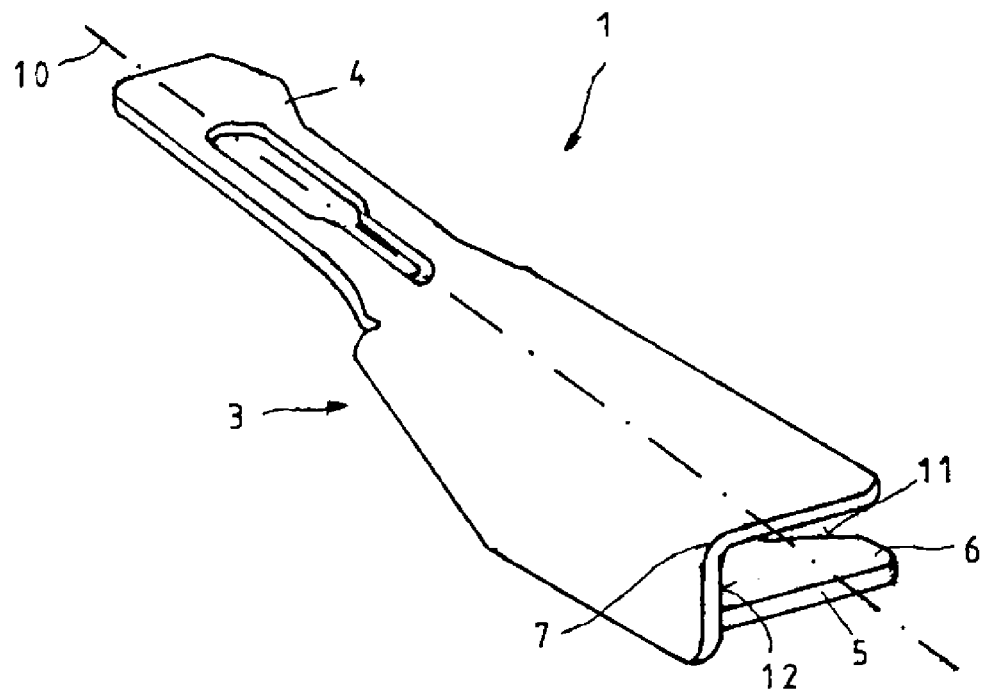
FIG. 2 shows a perspective view of the cutting instrument from FIG. 1, turned at an angle of 90 degrees.

FIGS. 1 and 2 show perspective views of a medical cutting instrument 1 for cutting muscles and tendons 2. This medical cutting instrument 1, serving for example as a tendon knife 1 consists essentially of an instrument body 3 on whose proximal end a handle 4 is positioned and that in the area of its distal end comprises at least one cutting knife 6 equipped with a cutting edge 5.

In the illustrated embodiment the part of the instrument body 3 that connects to the handle 4 on the distal end is configured as an L-shaped rectangular profile 7.

In the area of the cutting knife 5, the instrument body 3 has a grooved configuration in such a way that the instrument body 3 comprises a hollow space 8 that serves to receive and guide the muscle/tendon tissue 2 that is to be cut and that extends in the longitudinal direction of the instrument body 3, such that the instrument body 3 comprises an opening that extends in the longitudinal direction of the instrument body 3 and the cutting knife 6 constitutes one side of the instrument body 3.

As can further be seen from the drawings, the cutting knife 6 is positioned on the rectangular profile 7 of the instrument body 3 in such a way that the cutting edge 5 on the distal end is aligned perpendicularly to the instrument longitudinal axis 10 of the instrument body 3 and the instrument body 3 overlaps the cutting edge 5 of the cutting knife 6 by the distance a.

The configuration of a distance a between the distal end of the instrument body 3 and the cutting edge 5 ensures that the muscle/tendon attachment of the muscle/tendon tissue 2 that is to be cut is not harmed at the bone by the cutting knife 5.

Alternatively to the illustrated embodiment, in which the cutting knife 6 is positioned on the lower edge of the rectangular profile 7 of the instrument body 3, it is also possible to position the cutting knife 6 at a distance to the lower edge of the rectangular profile 7 of the instrument body 3. It is likewise possible to configure the cutting depth s formed by the distance between the cutting edge 5 and the lower side of the side of the rectangular profile 7 of the instrument body 3 opposite the cutting knife 6 so that it can be selected variably.

As a further alternative embodiment, it is possible to configure the instrument body 3 not as a rectangular profile 7 but rather with a curved cross-section.

To facilitate lateral incision of the tendon knife 1 into a tendon bundle that is to be cut, the cutting knife 6 overlaps the instrument body 3 in the direction perpendicular to the instrument longitudinal axis 10 by an overhang ü.

Figure 4:
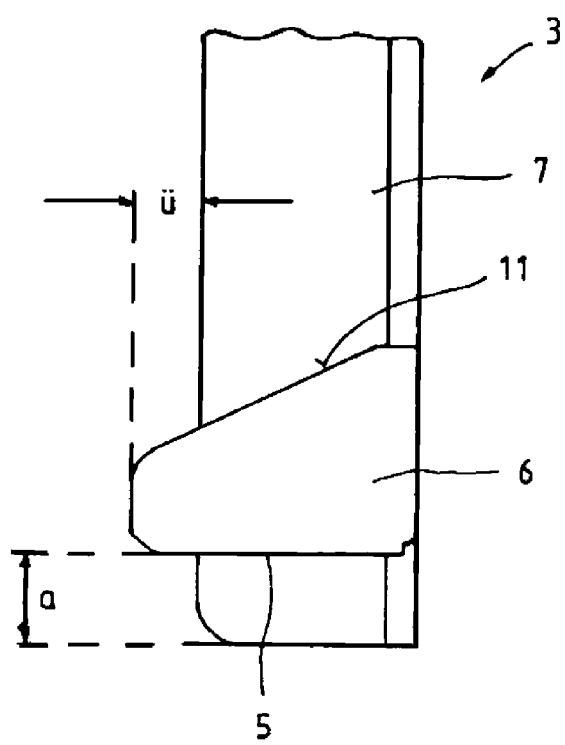
FIG. 4 shows a view from below of a distal end of the cutting instrument from FIG. 1.

In addition, as can be seen in particular from FIGS. 1 and 4, the proximal side 11 of the cutting knife 6 opposite the cutting edge 5 is configured as running perpendicularly toward the opening 9 of the instrument body 3.

Owing to the diagonal configuration of the side 11 of the cutting knife 6, the bundle of muscle/tendon tissue 2 into which the tendon knife 1 was incised with the overhang ü of the cutting knife 6 is conducted inward into the hollow space 8 surrounded on three sides, in such a manner that the inside of the instrument body 3 opposite the opening 9 of the instrument body 3 forms a guide surface 12 for the muscle/tendon tissue 2 that is to be cut.

A tendon knife 1 constructed as described is handled in the following manner.

Figure 3:
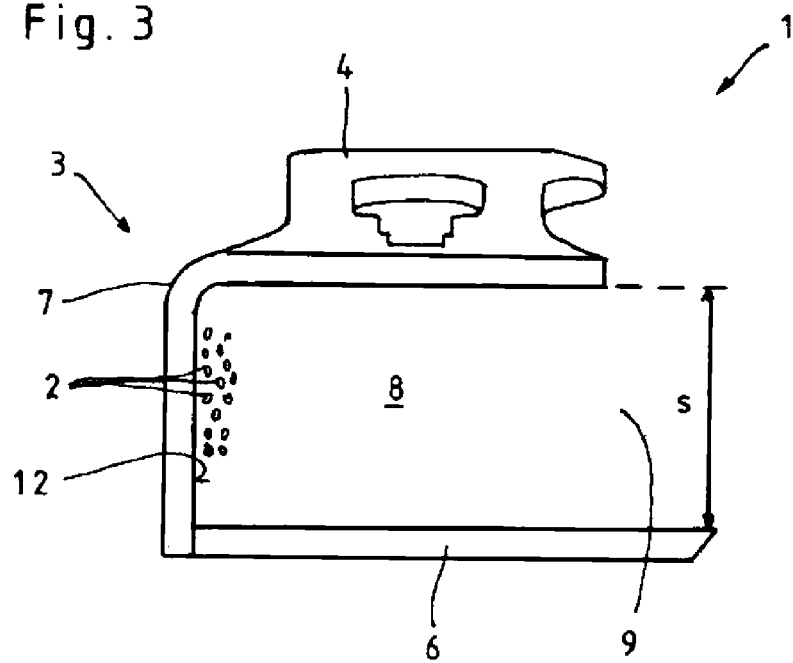
FIG. 3 shows a front view of the cutting instrument from FIG. 1.

The operator grips the tendon knife 1 on the proximal-end handle 4 and guides the cutting knife 6 with its overhang ü that overlaps the instrument body 3 in the fiber direction between or behind the fibers of the muscle or tendon tissue 2 that is to be cut, until the muscle or tendon tissue 2 is adjacent with the guide surface 12 in the inside of the hollow area 8 of the instrument body 3, as is shown schematically in FIG. 3. Guidance of the muscle or tendon tissue 2 all the way to the guide surface 12 is supported by the obliquely configured cutting knife edge 11.

As soon as the operator tips the tendon knife 1 out of its alignment in the fiber direction by 90 degrees into a position perpendicular to the fiber direction, he or she can cut through the muscle or tendon tissue 2 at the desired site by means of the cutting edge 5 of the cutting knife 6. The distance a of the cutting edge 5 from the distal end of the instrument body 3 thus prevents the muscle or tendon tissue 2 from being severed directly at the bone epiphysis.

A medical cutting instrument 1 configured in this way for cutting muscles and tendons 2 is characterized in that it ensures ease of operation and simple structure with a secure cutting of muscle/tendon tissue 2.

What is claimed is:

1. A medical cutting instrument for cutting muscles and tendons, with an instrument body that comprises a handle on its proximal end and at least one cutting knife in the area of its distal end, wherein the instrument body has a grooved configuration in the area of the cutting knife in such a way that the instrument body comprises a hollow space extending in the longitudinal direction of the instrument body to receive and guide the muscle or tendon tissue that is to be cut, such that the instrument body is configured as an L-shaped rectangular profile with a first side of the L-shape profile extending about the total length of the instrument body and defining the handle at its proximal end and with a second short side-wall of the L-shaped profile extending in the area of the cutting knife rectangular to the first side in the longitudinal direction of the instrument body, wherein the instrument body comprises an opening extending in the longitudinal direction of the instrument body and the cutting knife constitutes one side of the grooved configuration of the instrument body, wherein the cutting knife extends rectangular from the second short side-wall of the instrument body and parallel to the first side of the instrument body which extends about the total length of the instrument body, wherein the cutting knife overlaps a side of the grooved configuration of the instrument body opposite to the cutting knife in a direction perpendicular to the longitudinal axis of the instrument and wherein the cutting knife on the distal end comprises a cutting edge aligned perpendicularly to the longitudinal direction of the instrument body and the proximal side of the cutting knife that is opposite to the cutting edge is configured as running diagonally toward the open side of the grooved configuration of the instrument body, and wherein the hollow space is surrounded and circumscribed by wails on three sides, namely by the first side of the L-shaped profile, the second short side-wall of the L-shaped profile, and the knife.

2. The medical cutting instrument according to claim 1, wherein the instrument body overlaps the cutting edge of the cutting knife in the distal longitudinal direction of the instrument body.

3. The medical cutting instrument according to claim 1, wherein the cutting knife constitutes a side of the instrument body bordering the opening of the instrument body.

4. The medical cutting instrument according to claim 3, wherein the distance between the cutting knife and the first side of the instrument body that is opposite the cutting knife and borders the opening of the instrument body is adjustable.

5. The medical cutting instrument according to claim 1, wherein an inner surface of the second short side-wall of the instrument body that is opposite the opening of the instrument body forms a guide surface for the muscle or tendon tissue that is to be cut.

6. The medical cutting instrument according to claim 1, wherein the instrument body is configured with a curved cross-section.

7. The medical cutting instrument according to claim 5, wherein the guide surface is configured to be in contact with the muscle or tendon tissue that is to be cut.

* * * * *